(12) United States Patent
Olesinski et al.

(10) Patent No.: US 12,035,716 B2
(45) Date of Patent: Jul. 16, 2024

(54) TREATMENT FOR SEEDS DISINFECTION

(71) Applicant: VILMORIN & CIE, Paris (FR)

(72) Inventors: Amnon Olesinski, Motsa Ilit (IL);
Keith Kubik, Modesto, CA (US)

(73) Assignee: VILMORIN & CIE, Paris (FR)

( * ) Notice: Subject to any disclaimer, the term of this patent is extended or adjusted under 35 U.S.C. 154(b) by 341 days.

(21) Appl. No.: 14/900,390

(22) PCT Filed: Jul. 3, 2014

(86) PCT No.: PCT/EP2014/064237
§ 371 (c)(1),
(2) Date: Dec. 21, 2015

(87) PCT Pub. No.: WO2015/001043
PCT Pub. Date: Jan. 8, 2015

(65) Prior Publication Data
US 2016/0174557 A1    Jun. 23, 2016

(30) Foreign Application Priority Data

Jul. 4, 2013    (EP) .................................... 13305952

(51) Int. Cl.
*A01N 43/66*    (2006.01)
*A01C 1/08*    (2006.01)
*A61L 2/00*    (2006.01)

(52) U.S. Cl.
CPC ................ *A01N 43/66* (2013.01); *A01C 1/08* (2013.01); *A61L 2/0088* (2013.01)

(58) Field of Classification Search
CPC .......... A01N 43/66; A01C 1/08; A61L 2/0088
See application file for complete search history.

(56) References Cited

U.S. PATENT DOCUMENTS

| 2,932,128 A | 4/1960 | Porter et al. |
| 4,467,560 A * | 8/1984 | Simak ...................... A01C 1/00 |
| | | 209/11 |
| 2009/0305888 A1 | 12/2009 | Li et al. |
| 2010/0092442 A1* | 4/2010 | Jacobsen ................ A01N 63/00 |
| | | 424/93.46 |
| 2010/0154299 A1* | 6/2010 | Kobayashi ............... A01C 1/06 |
| | | 47/57.6 |

FOREIGN PATENT DOCUMENTS

| CN | 1124573 A | 6/1996 |
| CN | 1554236 A * | 12/2004 |
| CN | 102165883 A | 8/2011 |

(Continued)

OTHER PUBLICATIONS

Wiebe, Wayne L. et al., "BFB Bacterial Fruit Blotch", pp. 1-12.
(Continued)

*Primary Examiner* — Monica A Shin
(74) *Attorney, Agent, or Firm* — Oliff PLC

(57) ABSTRACT

The present invention relates to the treatment of plant material, especially seeds. The method uses vacuum pressure for disinfecting seeds from pathogens. Seed disinfection is important as seeds infected by pathogens could propagate them and lead to high losses of the crops. The method is applicable to seeds from cucurbit species specifically watermelon, melon, squash, pumpkin, cucumber and gourds but also seeds from solanaceous species specifically tomatoes, peppers and eggplants.

25 Claims, 1 Drawing Sheet

Industrial seed disinfection unit diagram:

1- Plexiglas reactor, octagon ~70L
2- disinfection solution + seeds
3- lid + seal
4- vacuum pipe + trap
5- vacuum pump
6- air inlet
7- pressure gauge
8- outlet valve
9- seed and solution collector
10- solution circulation pipe + pump
11- stand

(56) References Cited

FOREIGN PATENT DOCUMENTS

| | | | |
|---|---|---|---|
| EP | 1935245 A1 | 6/2008 | |
| JP | S63-222621 A | 9/1988 | |
| JP | S63-226215 A | 9/1988 | |
| JP | H01-312911 A | 12/1989 | |
| JP | H02-150290 A | 6/1990 | |
| JP | H03-035739 A | 2/1991 | |
| JP | H0343023 A | 2/1991 | |
| JP | 2006-204106 A | 8/2006 | |
| WO | 94/015448 A1 | 7/1994 | |
| WO | WO-9415448 A1 * | 7/1994 | ............... A01C 1/06 |
| WO | 2008/092017 A1 | 7/2008 | |
| WO | WO-2011115798 A2 * | 9/2011 | ......... A01N 2300/00 |

OTHER PUBLICATIONS

Docea, E. et al., "Contribution to the control of the bacterial canker of tomato caused by corynebacterium michiganese (E,F, Smith) Jensen" Acta Horticulturae (May 1977) pp. 469-474.

Dutta, B. et al., "Location of Acidovorax citrulli in Infested Watermelon Seeds Is Influenced by the Pathway of Bacterial Invasion" Phytopathology (2012) vol. 102, No. 5, pp. 461-468.

Flood, J. et al., "Eradication of Fusarium from oil palm by seed treatments" (1994) BCPC Monograph No. 57:—Seed Treatment: Progress and Prospects, pp. 201-205.

Zuckerbraun, Eliezer, "Third Party Observation for Application No. WO2014EP64237" (Jul. 26, 2015) pp. 1-2.

Frank, T. "Disinfecting Nepenthes Seeds" (Oct. 15, 2011) pp. 1-10.

Frare, Vanessa C. "Melon (*Cucumis melo* L.) seeds treatment to control *Acidovorax avenae* subsp. *citrulli*" (2010) Abstract.

Gaba, Victor "Stabile chlorine compounds in solid form" (Oct. 25, 2001) pp. 1-2.

Maude, R.B et al.,"Investigation and control of seedborne *Colletotrichum* spp. causing anthracnose of lupins and lavatera" (1994) pp. 1-18.

Jan. 5, 2016 International Search Report issued in International Patent Application No. PCT/EP2014/064237.

* cited by examiner

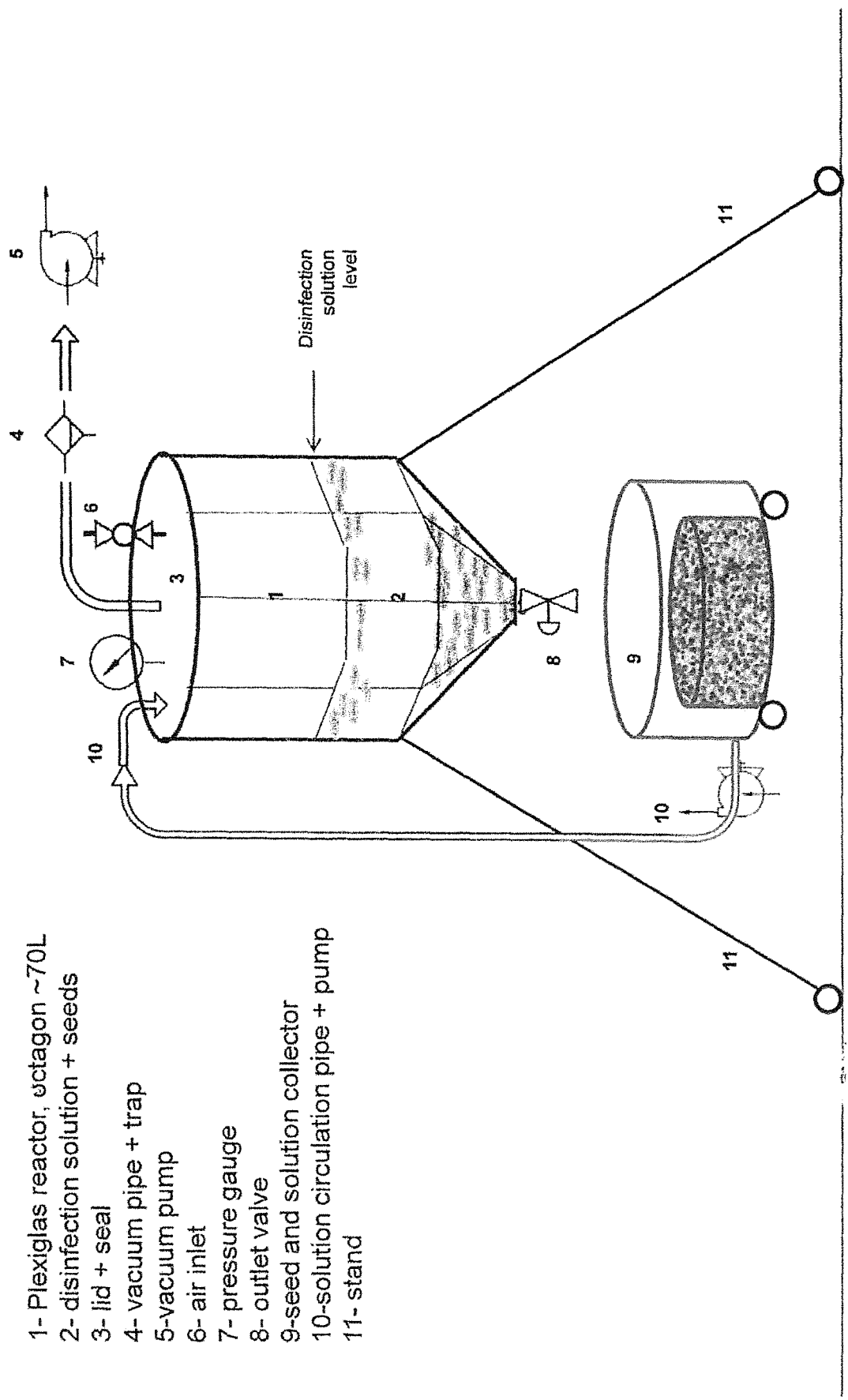

TREATMENT FOR SEEDS DISINFECTION

FIELD OF THE INVENTION

The present invention relates to the treatment of seeds. The method uses vacuum pressure for disinfecting seeds from pathogens, such as fungi, bacteria, viruses, viroids, virus-like organisms, oomycetes, phytoplasmas, protozoa, nematode and the likes. The method is applicable for example to seeds from cucurbit species specifically watermelon, melon, squash, pumpkin, cucumber and gourds or seeds from solanaceous species, specifically tomatoes, peppers and eggplants.

BACKGROUND OF THE INVENTION

Seed-borne pathogens cause every year important economic losses. In particular, they reduce the crop yield, deteriorate its quality and make storage of vegetables more difficult. For cultivators, it is therefore essential to receive seeds free from pathogens, since control is difficult to effect during the cultivation season.

In general, seeds are subjected to various treatments in order to kill the pathogens present on the seeds so that the transmission of pathogens to the crop to grow from the seeds is avoided and harm to the seeds themselves is prevented. Such treatment may also increase the storage life of seeds. This applies to both seeds for sowing and seeds which are, possibly after germination, suitable for consumption or industrial processing. For seeds intended for reproduction or for consumption or industrial processing after the start of germination process, it is logically of vital importance that the germination capacity, or the enzyme activity, is preserved.

Seed disinfection needs to eradicate external and internal seed-borne diseases without negatively affecting the seed characteristics such as viability, germination and speed of emergence as well as final stand of the plants. Seed disinfection can be performed by various techniques that range from chemical to physical ones.

Chemical products such as peroxyacetic acid, hydrochloric acid or sodium hypochlorite can reduce for example seed borne *Acidovorax citrulli* inoculum, but they generally fail to eradicate the bacterium from the infected seeds (Dutta, B, Avci, U, Hahn, M. G. and Walcott R. R. 2012. *Phytopathology* 102/5 461-468).

Other means such as hot water immersion or use of hot humid air are currently used, but they do not work properly on all seeds and might lead to some seed defects.

A combination of chemical and physical means such as vacuum infiltration of chemicals is also known. The goal of such technique is to bring the disinfecting products closer to the pathogens, whether still outside of the seed or directly inside it. See for example WO94/15448 where vacuum infiltration is applied to oil palm seeds (Flood et al Gitaitis, R. D., and Walcott, R. R. 2008. *Annu. Rev. Phytopathol.*, 45:371-397; Nagy et al). See also Docea et al, May 1976, *Acta Horticulturae, International Symposium Bucharest*, 58/1977, where tomato seeds are disinfected from *Corynebacterium michiganense* by vacuum infiltration with cryptonol.

It has however to be noted that in all these studies, the seeds have been artificially infected, which makes an essential difference from seeds naturally infected. Indeed, artificial infection is done on matured seeds and is therefore usually only superficially contaminating the seed. As such, the contact between the disinfecting chemical solution and the pathogen located outside the seed is relatively easy to achieve, thereby apparently efficiently disinfecting the artificially inoculated seed. However, naturally infection of *Acidovorax citrulli* and other such seed-borne pathogens starts as early as at flower stage, which is the very first stage of seed setting. At this stage, the infection reaches the very deep parts inside the seed that will be later unreachable by the standard wet seed disinfection (Dutta, B, Avci, U, Hahn, M. G. and Walcott R. R. 2012. *Phytopathology* 102/5 461-468).

Therefore, while these various disinfection techniques appear of interest, they may not be efficient enough for producing seed lots of commercial quality, i.e. seed lots where the pathogen had been inactivated. The seed lots could remain infected on levels that make them unsalable, or subject to cautions and legal disclaimer. They may have to be destroyed, causing money losses to the seed companies or growers.

It would therefore be of interest to develop a new process for disinfecting seeds and obtaining seed lots of commercial value free from infectious pathogens.

SUMMARY OF THE INVENTION

The purposes of the invention are achieved by a method of disinfecting seeds comprising:
  a) placing the seeds and a disinfecting solution into a vacuum reactor; wherein the seeds are submerged into the disinfected solution either prior or after the step b),
  b) applying a vacuum pressure;
  c) releasing the vacuum pressure;
  d) reiterating the steps b-c, at least once;
  e) separating the sinking fraction of the seeds from the floating fraction; wherein said sinking fraction contains disinfected seeds.

Preferably, the steps b-c are reiterated until no new sinking fraction is observed at step c. In one embodiment, the sinking fraction is collected after each cycle of steps b-c.

In another embodiment, performing steps a-e takes no more than 2 hours, preferably no more than 1 hour, and more preferably no more than 30 minutes. In another embodiment, vacuum pressure applied at step b is comprised between 400 and 985 mbar, preferably between 500 and 980 mbar, most preferably between 400-500 and 975-985 mbar. In another embodiment, the plurality of cycles of steps b-c is carried out with increasing the vacuum pressure at each cycle, for example the vacuum pressure is increased by 100 mbar after each cycle of steps b-c. These parameters of vacuum pressure will be determined by the skilled person, for example the maximum vacuum pressure to be applied could range from 975 to 985 mbar and the increasing steps in vacuum pressures can be of 10, 20, 30, 40, 50, 60, 70, 80, 90, 100, 110, 120, 130, 140, 150, 160, 170, 180, 190, 200, 210, 220, 230, 240, 250, 260, 270, 280, 290, 300 mbar and any vacuum pressure in between. Further, the increasing step might be equals, for example the vacuum pressure is increased by 50 mbar after each cycle of steps b-c, or might be un-regular, for example, the vacuum pressure is increased by 50 mbar after a first cycle of steps b-c, by 60 mbar after a second step of b-c, by 70 mbar after a third step of b-c etc.

In one preferred embodiment, the seeds are from cucurbit species, more specifically selected from the group consisting of watermelon, melon, squash, pumpkin, cucumber, and gourd species, or solanaceous crops, more specifically selected from the group consisting of tomatoes, peppers and eggplants species. In another embodiment, the disinfecting solution may be a chemical agent that destroys any pathogen, for example fungi, bacteria, viruses, viroids, virus-like organisms, oomycetes, phytoplasmas, protozoa and/or nematode, for example a solution containing at least 0.1%, 0.2%, 0.3%; 0.4%, 0.5%, 0.75%, 1%, 1.5%, 2%, 3%, 4%, or 5% of Na-dichloroisocyanurate, sodium hypochlorite, or calcium hypochlorite.

The invention can be advantageously applied to seeds that are naturally infected by pathogens. By "seeds that are naturally infected by pathogens", it is meant that the seeds are infected by the pathogens during the formation of the seeds in or on the plant. Such pathogens that infect seeds during their formation are commonly called seed-borne pathogens. Examples of seed-borne pathogens are: (i) *Pseudomonas savastanoi* pv. *phaseolicola* and *Xanthomonas axonopodi* pv. *phaseoli* in Bean, (ii) *Phoma lingam* and *Xanthomonas campestris* pv. *campestris* in *Brassica*, (iii) *Alternaria dauci, Alternaria radicina, Alternaria radicina* and *Xanthomonas hortorum* pv. *carotae* in Carrot, (iv) *Septoria apiicola* in Celery, (v) *Acidovorax valerianellae* in Cornsalad, (vi) *Acidovorax* spp., *Acidovorax avenae* subsp. *citrulli*, Squash mosaic virus, Cucumber green mottle mosaic virus, Cucumber fruit mottle mosaic virus and Melon necrotic spot virus in Cucurbit, (vii) Lettuce mosaic virus in Lettuce, (viii) Pea seed-borne mosaic virus, Pea early browning virus and *Pseudomonas syringae* pv. *pisi* in Pea, (ix) Tobamoviruses and *Xanthomonas* spp. in Pepper, (x) *Clavibacter* spp., *Clavibacter michiganensis* subsp. *michiganensis*, Pepino mosaic virus, Tobamoviruses, *Pseudomonas* spp. and *Xanthomonas* spp. in Tomato.

The invention also relates to a method of producing seeds essentially free from pathogens, e.g. free from seed-borne pathogens, comprising the steps of:
a. providing seeds;
b. treating said seeds by applying the disinfecting method of the present invention; and
c. recovering said treated seeds as seeds essentially free from viable pathogens.

The invention further concerns the seeds obtained or obtainable by the above producing method. The invention further relates to seeds essentially free from viable pathogens, e.g. free from seed-borne pathogens, containing the disinfecting solution such as the Na-dichloroisocyanurate, sodium hypochlorite, or calcium hypochlorite. The invention can be advantageously applied to seeds selected from the group consisting of cucurbit and solaneaceouse species, more specifically, watermelon, melon, squash, pumpkin, cucumber, gourd, tomatoes, peppers and eggplants species.

In another aspect, the invention relates to a solution comprising Na-dichloroisocyanurate for use as disinfecting agent to treat seeds. In a specific embodiment, said solution is introduced into the seeds by vacuum infiltration. In another aspect, the invention relates to a solution comprising Na-dichloroisocyanurate for use as disinfecting agent to treat seeds that have been externally infected. These solutions contain for example, at least 0.1%, 0.2%, 0.3%, 0.4%, 0.5%, 0.75%, 1%, 1.5%, 2%, 3%, 4%, or 5% of Na-dichloroisocyanurate.

In yet another aspect, the invention relates also to a device for carrying out the disinfecting method of the invention, comprising
 i. a reactor including a chamber which can be sealed for applying vacuum pressure inside the chamber,
 ii. means for applying vacuum pressure in the reactor chamber,
 iii. means for collecting the sinking fraction of seeds,
 iv. means for releasing the vacuum pressure,
 v. means for separating the disinfecting solution from the collected sinking fraction of seeds, and reintroducing the collected disinfecting solution into the reactor chamber,
 vi. optionally, means for introducing the seeds in the solution only after the desired vacuum pressure is applied.

BRIEF DESCRIPTION OF THE DRAWINGS

FIG. 1 illustrates one example of a reactor according to the invention.

DETAILED DESCRIPTION OF THE INVENTION

Accordingly, the present invention provides a two-step method based on a first step vacuum infiltration of disinfecting solution further completed by a selection step of the sinking fraction.

More specifically, the invention relates to a method of disinfecting seeds comprising:
a) placing the seeds and a disinfecting solution into a vacuum reactor; wherein the seeds are submerged into the disinfected solution either prior or after the step b),
b) applying a vacuum pressure;
c) releasing the vacuum pressure;
d) reiterating the steps b-c, at least once;
e) separating the sinking fraction of the seeds from the floating fraction; wherein said sinking fraction contains disinfected seeds.

Any kind of seeds may be treated according to the methods of the invention. For example, seeds may include seeds of both monocotyledonous and dicotyledonous plants that may be useful for agronomic, horticultural, or ornamental purposes. Particularly, important groups of plants that provide seeds which may be treated with the methods of the invention are the vegetables, the cereals and grasses. The cereals include, but are not limited to, wheat, triticale, barley, rye, rice, and oats. The grasses include the sod and forage grasses, such as brome grass, blue grass, tall fescue grass, and Bermuda grass. Other grasses are the tropical grasses, such as sugar cane, corn, millet, and sorghum. Vegetables include solanaceous plants and cucurbits. Solanaceous seeds, such as potatoes, tomatoes, tobacco, eggplant, and pepper seeds are appropriate seeds to be treated according to the methods of the invention, as are Brassicaceae seeds, such as cauliflower, broccoli, cabbage, kale, and kohlrabi. Other suitable seeds include those of carrots, parsley, sugar beets, cotton, fruit trees, berry plants, and grapes seeds. In addition, the methods of the invention may be used for seeds of tree species, such as pine, spruce, fir, aspen and the various hardwoods. Seeds of the Gramineae, Leguminosae, and Malvaceae families may also be used. Particularly the method is used to treat seeds as listed in Annex to chapter 5, International Rules for Seed Testing, International Seed Testing Association, Zurich, Switzerland, 1996.

In one embodiment, the invention may be applied to seeds from cucurbits, more specifically selected from the group of watermelon, melon, squash, pumpkin, cucumber, and gourd species or Solanaceae more specifically selected from the group of tomatoes, peppers and eggplants species. Preferably, disinfecting seeds of cucurbits or Solanacea contain a disinfecting solution sufficient to render the seed essentially free of any viable pathogen, e.g. seed-borne pathogen, such that the seed can meet quarantine regulations.

Preferably, the methods may be applied to seeds naturally infected by pathogens, i.e. seeds infected by seed-borne pathogens. In the case of cucurbits seeds more specifically selected from the group of watermelon, melon, squash, pumpkin, cucumber, and gourd species, the most important seed-borne bacterial infection is caused by *Acidovorax* spp. more specifically *Acidovorax citrulli*; the most important seed-borne viral infection is caused by species of genus Tobamovirus, more specifically Cucumber green mottle mosaic virus (CGMMV) or Cucumber fruit mottle mosaic virus (CFMMV). For the solanaceous seeds more specifically selected from the group of tomatoes, peppers and eggplants species, the most important seed-borne bacterial infection is caused by *Clavibacter* spp more specifically *C. michiganensis*, even more specifically *C. michiganensis* subsp. *michiganensis, Pseudomonas* spp, *Xanthomonas* spp; the most important seed-borne viral infections are caused by TMV, PepMV. Viroids could also cause infections.

In some embodiments, the method according to the invention allows the production of a seed lot in which at least 90, 95, 96, 97, 98, 99 or 100% of the seeds are disinfected. In a particular preferred embodiment, the method according to the invention allows the production of a seed lot in which 100% of the seeds are disinfected.

In some embodiments, the method according to the invention allows the production of disinfected seeds without affecting their germination quality. In some embodiments, the obtained disinfected seeds have a germination rate of at least 85, 86, 87, 88, 89, 90, 91, 92, 93, 94, 95, 96, 97, 98, 99, or 100%. In a particular preferred embodiment, obtained disinfected seeds have a germination rate of 100%. In other words, the method according to the invention allows the production of a seed lot in which at least 90, 95, 96, 97, 98, 99 or 100% of the disinfected seeds germinate. In a particular preferred embodiment, the method according to the invention allows the production of a seed lot in which 100% of the disinfected seeds germinate.

The Vacuum Infiltration Step

The step of vacuum infiltration of the method of the invention is aimed at infiltrating a disinfectant agent contained in the disinfecting solution, into the seeds. It is carried out by applying a vacuum to remove air from spaces in the seed tissue, contacting the seeds (by submersion) with a disinfecting solution and releasing the vacuum. In one first embodiment, the seeds to be treated are submerged into the disinfecting solution prior to applying vacuum pressure. Without being bound by any theory, it is then believed that the free spaces in the seed are filled by the disinfecting solution.

The initial vacuum pressure applied to the seeds submerged by the disinfecting solution may be set up between 400-500 and 975-985 mbar, for example between 550 mbar and 700 mbar, or between 700 and 820 mbar, still for example between 576 and 667 mbar or between 740 to 816 mbar. Preferably the vacuum step is carried out by first applying a vacuum pressure comprised between 400-700 mbar, preferably 400-600 mbar. The vacuum is then released immediately or after a period comprised between 1 second to 5 minutes, preferably after a vacuum period less than 2 minutes, preferably less than 1 minute. These parameters of time and vacuum pressure will be easily determined by the skilled person depending, inter alia, on the type of seeds and the amount of seeds.

When introduced in the disinfecting solution, preferably an aqueous solution, part or all seeds may initially float. Without being bound by any theory, it is believed that, at each cycle step of vacuum/de-vacuum, the solution is forced by pressure differences into the air-evacuated spaces of the seed tissues which may cause the seeds to sink. As the solution contains disinfectant product(s), the penetration of the solution into the seed air spaces cleared by the vacuum may improve the contact between the solution and surface of the pathogens, and increases the effectiveness of the disinfection treatment. This step cycle of vacuum/de-vacuum is typically repeated at least once, to increase the efficiency of the method. Preferably it is repeated until no new sinking fraction is observed after release of the vacuum pressure. As used herein, a "sinking fraction" refers to a fraction of seeds which has a density that is superior to water or the aqueous solution.

When repeating vacuum/de-vacuum cycles, advantageously, the vacuum pressure is increased at each cycle, for example, the vacuum pressure is increased by 100 mbar after each cycle of vacuum/de-vacuum. These parameters of vacuum pressure will be determined by the skilled person, for example the maximum vacuum pressure to be applied could range from 975 to 985 mbar and the increasing steps in vacuum pressures can be of 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 350, 400, 450, 500, 550, 600, 650, 700, 750 mbar and any vacuum pressure in between. Further, the increasing step might be equals, for example the vacuum pressure is increased by 50 mbar after each cycle of steps b-c, or might be un-regular, for example, the vacuum pressure is increased by 50 mbar after a first cycle of steps b-c, by 60 mbar after a second step of b-c, by 70 mbar after a third step of b-c etc.

The specific vacuum pressures and timing of each vacuum/de-vacuum steps are determined in order to obtain two fractions of seeds, one sinking fraction and one floating fraction. The skilled person will determine the specific conditions to obtain a sufficient amount of sinking seeds, preferably within a minimum period of time.

Typically, equivalents of about 1 kg of seeds are submerged in 5-10 liters of disinfecting solution, such as Na-dichloroisocyanurate, for example 0.1% dichloroisocyanurate, 0.1% of sodium hypochlorite, or 0.1% of calcium hypochlorite, and a vacuum pressure is first applied at a pressure comprised between 400-700 mbar, preferably 400-600 mbar, then the vacuum pressure is released after a period of less than 2 minutes, preferably 1 minute and vacuum pressure is again applied, preferably at increasing vacuum pressure, for example until the vacuum pressure reaches the maximum level possible in a sealed space containing aqueous solution, namely 975-985 mbar.

As used herein, the term "disinfecting solution" means any solution comprising a disinfecting agent, for example, chemical agent, that destroys harmful organisms, i.e. any pathogen. The solution is preferably an aqueous solution. Any known fungicides and germicides such as antibiotics, antibacterials, antivirals, antifungals, antiprotozoals and antiparasites and other disinfecting agent for plant material, preferably seeds, may be used with the methods of the invention. Examples of disinfectant agent include, without limitation, Bromine, Chlorine, Chlorite, Iodine, Hydrogen Peroxide, Potassium Permanganate, Hydrochloric acid, Peracetic acid, Peroxiacetic acid, Sulfuric Acid, Phosphoric Acid, Formaldehyde, Glutaraldehyde, Sodium Hydroxide, Phenol, Peroxomonosulphate, Tri Sodium Phosphate, Quaternary Ammonium, Silver and Copper (ionic or salts), Iodine, Bromine, Triclosan, etc. In a preferred embodiment, the disinfecting solution contains a chlorine based disinfecting agent, such as Na-dichloroisocyanurate, sodium hypochlorite or calcium hypochlorite. In a preferred embodiment, the disinfecting solution contains Na-dichloroisocyanurate as disinfecting agent, already known to be used to keep cut flowers in vases. In another preferred embodiment, the disinfecting solution contains sodium hypochlorite or calcium hypochlorite as disinfecting agent. Preferably, the disinfecting solution is an aqueous solution with at least 0.1%, 0.2%, 0.3%, 0.4%, 0.5%, 0.75%, 1%, 1.5%, 2%, 3%, 4%, or 5% of Na-dichloroisocyanurate, sodium hypochlorite, or calcium hypochlorite. Preferably, the disinfecting solution is an aqueous solution with a concentration of Na-dichloroisocyanurate, sodium hypochlorite, or calcium hypochlorite comprised between 0.1% to 2%, preferably between 0.25% to 2.5%, still preferably between 0.5% to 2%.

Alternate Vacuum Infiltration Step

In a second embodiment of the vacuum infiltration step of the method of the invention, the seeds and the disinfecting solution are placed into the vacuum reactor but the seeds are not put into contact with the disinfecting solution prior to applying vacuum pressure. For example, the seeds may be maintained in a basket above the disinfecting solution into the reactor chamber prior to application of vacuum pressure. Then the basket is lowered to submerge the seeds into the disinfecting solution.

The rest of the method is carried out as described for the first embodiment.

Typically, equivalents of about 1 kg of seeds may be held in a basket above the disinfecting solution, the vacuum pressure is applied at a pressure comprised between 400-700 mbar, preferably 400-600 mbar, and the seeds are then submerged in 5-10 liters of disinfecting solution, such a Na-dichloroisocyanurate, sodium hypochlorite, or calcium hypochlorite, for example 0.1% Na-dichloroisocyanurate, 0.1% sodium hypochlorite, or 0.1% calcium hypochlorite, then the vacuum pressure is released after a period of less than 2 minutes, preferably less than 1 minute, and vacuum pressure is again applied, preferably at increasing vacuum pressure.

The Selection Step

It is to the credit of the inventors to have realized that the sinking behavior of treated seeds actually reflects the extent of penetration of the disinfecting solution into the seed materials and provide convenient means to visualize the efficiency of the disinfecting process and to sort out the treated seeds from the non-treated seeds.

Accordingly, the second step of this process aims at separating the seed fraction that remains floating from the seed fraction that is sinking, either by discarding a seed fraction that remains floating after vacuum infiltration step and/or by collecting the sinking fraction.

The floating seeds are indeed presumed to have not absorbed sufficient amount of the disinfecting solution, therefore still presenting sanitary risks of remaining pathogens. In addition, collecting the sinking fraction or discarding the floating fraction surprisingly appears to benefit overall seed lot germination quality, thereby allowing the production of a seed lot in which at least 90, 95, 96, 97, 98, 99 or 100% of the seeds are disinfected, and more preferably allowing the production of a seed lot in which 100% of the seeds are disinfected.

In some embodiments, the sinking fraction contains at least 90, 95, 96, 97, 98, 99 or 100% of disinfected seeds, and more preferably 100% of disinfected seeds. In some embodiments, the seeds of the sinking fraction have a germination rate of at least 85, 86, 87, 88, 89, 90, 91, 92, 93, 94, 95, 96, 97, 98, 99, or 100%. In a particular preferred embodiment, the seeds of the sinking fraction have a germination rate of 100%.

The sinking fraction may be collected after each cycle of vacuum/de-vacuum or at the end of the process. For some seeds, the sinking fraction might be the only fraction, i.e., there is no floating fraction of seeds.

In the second step of the present invention, the separation of the floating fraction is preferably fast, typically within a few minutes, for example between 1 second to 5 minutes, for example less than 2 minutes, preferably less than 1 minute. Preferably, the method of the present invention does not comprise any soaking step, such as those soaking steps described in WO94/15448, especially it may not comprise any soaking step of more than 12 hours.

Advantageously, the entire method from seeds submersion to the seeds collecting preferably takes no more than 2 hours, preferably even no more than 1 hour, and more preferably no more than 30 minutes.

After collection, the seeds may be washed and dried. The seeds may further be treated with alternative treatments for seed decontamination or protection. For example, other conventional seed treatments may be applied, via coating, pelleting, or film-coating, especially in order to prevent seed or plantlet damage, including without limitation fungicides or insecticides treatments.

Methods of Producing Seeds Essentially Free from Viable Pathogens

In a second aspect, the present invention provides a method for producing seeds essentially free from viable pathogens, e.g. free from viable seed-borne pathogens, comprising the steps of:
a) providing seeds;
b) treating said seeds by applying the disinfecting method of the invention, and
c) recovering said treated seeds as seeds essentially free from viable pathogens.

As used herein, a seed "essentially free from pathogens" or "essentially free from viable pathogens" is a seed which, after germination, will not develop any infectious disease in a sterile environment. In one embodiment, a seed "essentially free from pathogens" or "essentially free from viable pathogens", both being interchangeably used, is a seed which does not contain any of the following infective elements in viable form or in infective form: fungi, bacteria, viruses, viroids, virus-like organisms, oomycetes, phytoplasmas, protozoa, and/or nematode. Said method typically comprises the steps of (i) providing seeds, (ii) treating said seeds by applying the disinfection method as described above and (iii) recovering said treated seeds as seeds essentially free from pathogens. In some embodiments, the seeds produced by such a method are "essentially free from viable seed-borne pathogens" or "essentially free from seed-borne pathogens".

The seeds obtained or obtainable by this production method, are characterized in that (i) they are essentially free from viable pathogens, and (ii) they contain the disinfecting solution, such as Na-dichloroisocyanurate, sodium hypochlorite or calcium hypochlorite.

The invention therefore relates to seeds essentially free from viable pathogens, and containing the disinfecting solution, such as Na-dichloroisocyanurate, sodium hypochlorite or calcium hypochlorite. Preferably, such seeds are selected from the group consisting of cucurbits, and solanaceous species, more specifically watermelon, melon, squash, pumpkin, cucumber, gourd, tomatoes, peppers and eggplants species.

The invention also relates to the use of Na-dichloroisocyanurate as disinfecting agent to treat seeds. In one embodiment, said Na-dichloroisocyanurate has been introduced into the seeds by vacuum infiltration, for example, at a concentration of at least 0.1%, 0.4%, 0.75%, 1%, 1.5%, 2%, 3%, 4%, or 5%.

It is also to the credit of the inventors to have realized that the Na-dichloroisocyanurate, so far known to be used to keep cut flowers in vases, can be used to disinfect seeds. Further, and contrary to all the other disinfecting solutions known as of today, the Na-dichloroisocyanurate preserves and in some cases even improves seed germination quality.

Device for Carrying Out the Methods of the Invention

The invention also relates to devices for carrying out the methods of the invention.

In one embodiment, a device for carrying out the disinfecting method of the invention, comprises
i. a reactor comprising a chamber which can be sealed for applying vacuum pressure inside,
ii. means for collecting the sinking fraction of seeds,
iii. means for applying vacuum pressure inside the reactor chamber,
iv. means for releasing the pressure,
v. optionally, means for separating the disinfecting solution from the collected sinking fraction of seeds, and reintroducing the collected disinfecting solution into the reactor chamber,
vi. optionally, means for introducing the seeds into the solution after the desired vacuum pressure has been applied.

FIG. 1 illustrates one example of a reactor according to the invention.

The reactor (1) of the device may be any reactor with a chamber for containing the seeds submerged in the disinfecting solution (2) and resistant to vacuum (also referred to as the vacuum chamber). Typically, it may be made in Plexiglas or other material resistant to vacuum pressure, and preferably transparent for visualizing the behavior of the seeds during the process (sinking or floating). For example, the reactor chamber may contain between 10-50 liters of volume of disinfecting solution with seeds, in 70 L liters Plexiglas reactor.

The reactor may contain a lid (3), preferably in its upper part, which can be opened for introducing the seeds and/or disinfecting solution and can be closed hermetically to allow applying vacuum pressure within the reactor chamber.

The device may further contain a vacuum pipe (4), for example connected to the lid, on the upper side of the reactor, and a vacuum pump (5) to apply vacuum pressure within the reactor chamber. Advantageously, the reactor further contains a pressure gauge (7) and/or means for controlling the vacuum pressure within the reactor chamber and/or means for releasing the vacuum (6). Alternatively, the floating fraction can be collected from the upper part of the solution by means of using a strainer or by rotating the chamber and discarding the floating seeds to another container from the top of the vessel.

The reactor is preferably elevated, for example with stands (11) and comprises an outlet valve, for example, in its lower part, for evacuating the sinking fraction of seeds (8) and collecting it in the collector (9), the collector being placed for example under the reactor chamber. The collector may include a container with perforated walls (or semipermeable) so that the seeds are contained in the container and the collected disinfecting solution may move outside the container. Advantageously, the device further includes means (for example with a pipe and pump) for extracting the collected disinfecting solution from the collector and reintroducing it into the reactor chamber (10).

In specific embodiments, the vacuum pipe (4) may also further contain a trap.

Specific embodiments of the invention will now be illustrated in the following examples.

EXAMPLES

Example 1: Disinfection of Watermelon Seeds Naturally Infected by Bacterial Fruit Blotch Bacterial Fruit Blotch (BFB) is a disease caused by the bacteria *Acidovorax citrulli* that can be devastating for farmers as fruit losses can reach more than 90% of a production field. According to Walcott, R. R. 2005. *The Plant Health Instructor*. DOI: 10.1094/PHI-I-2005-1025-02—http://www.apsnet.org/edcenter/intropp/lessons/prokatyotes/Pages/BacterialBlotch.aspx. Bacterial fruit blotch (BFB) affects the foliage at all growth stages and fruit of a wide range of cucurbitaceous hosts. Symptoms such as water-soaking on the undersides of cotyledons can be initially observed on cucurbit seedlings, between five and eight days after planting. BFB-associated lesions have a greasy appearance and persist under dry conditions, i.e., observable after mid-day. Water-soaked lesions start as discrete spots but then coalesce and extend along the veins of the cotyledons. They eventually dry to form elongated, dark to reddish-brown lesions that develop on and along cotyledon veins. Similar symptoms are produced on melon and other cucurbit seedlings. On mature watermelon foliage, distinct dark to reddish-brown lesions develop along leaf veins. The economic loss results from the fruit rot phase of the disease. Indeed, BFB symptoms on watermelon fruits appear just prior to harvest maturity as small (<1 millimeter in diameter), irregularly-shaped, olive-colored spots on the upper surfaces of the fruit. These lesions, although initially small, can spread and cover the entire upper surface of the fruit. At early stages of infection these lesions are firm and rarely penetrate into the flesh of the fruit. Brown cracks may develop in the rind lesions. At advanced stages, fruits collapse into a watery rot due to invasion by secondary colonizing organisms.

The management of BFB infestation in production is extremely difficult. Preferably, seeds are only produced in areas without any record of BPB presence, with field rotations. According to Walcott, "no chemical or physical seed treatments are 100% effective at eradicating *A. avenae* subsp. *Citrulli*". While seed treatments including thermotherapy, NaOCl, fermentation, HCl and peroxyacetic acid significantly reduce BFB seedling transmission, they can adversely affect seed physiology. Two factors that influence seed treatment efficacy are: 1) the inability of seed treatments to penetrate the seed coat, and 2) location of bacteria on/in the seed. Because the risk of BFB development in transplant houses is high for seed with low levels of infestation, seed treatment alone cannot control BFB".

Therefore, as of today, it is believed that chemical disease management and seed health testing have limited effect: while it is possible to detect heavily infested seed lost, the lots with very low infestation are difficult to identify.

Generally, seed companies are testing between 30,000 to 50,000 seeds per seed lot (Gitaitis, R. D., and Walcott, R. R. 2008. *Annu. Rev. Phytopathol.*, 45:371-397) which represents a heavy burden both in terms of time and of money as a seed lot can be accepted when none of the 30,000 or 50,000 seeds has been tested positive. Even with such a large sample, seed companies and growers still face a threat as seed lots can be infected by such a low level which is undetectable at 50,000 seed sample.

In the present case, 0.2 kg of watermelon seeds was obtained from a commercial seed lot, naturally infected by BFB in the production field. After a standard disinfection process of 1.0% Na-Dichloroisocyanurate, they were still infected. Dry seeds with standard Moisture Content of 5.5-7.5% are put in a 10 liter glass vessel together with 1.0 liters of disinfecting solution comprising of Na-Dichloroisocyanurate at 0.2%. A vacuum is applied and build up to about 500 mbar then released. This process of vacuum/de-vacuum is repeated, each time with an increase of the vacuum pressure by approximately 100 mbar, up to the maximum reachable vacuum pressure of about 975-985 mbar. This process leads to the formation of two seed fractions in the vessel: one sinking fraction and one floating fraction. The floating fraction of the seeds is collected and the vacuum process applied again on it. The vacuum cycles continue until floating seeds are no longer sinking. The floating seeds are then removed and discarded. This process takes 20-30 minutes.

The seeds that sunk are then washed at running water during 10 minutes and dried. These seeds have been disinfected from BFB. They are further easily identifiable because the inside of the seed still contains traces of the disinfecting product.

4200 seeds were tested and found negative for BFB by sweat box assay (see reference below).

Example 2: Disinfection of Melon Seeds Naturally Infected by Bacterial Fruit Blotch 49 kilograms of melon seeds naturally infected by BFB where disinfected twice by a standard disinfection protocol (Na-Dichloroisocyanurate, 1% and 2% concentration; duration: 10 min; rinse 10 min). The disinfected seed were then tested for BFB and found still heavily infested. Batches of 4.5 kilograms of this seed lot were put in a 70 liter reactor (as described in FIG. 1) together with 20 liters of disinfecting solution comprising of Na-Dichloroisocyanurate at 0.5%.

A vacuum is applied and build up to about 500 mbar then released. This process of vacuum/de-vacuum is repeated, each time with an increase of the vacuum pressure by approximately 100 mbar, up to the maximum reachable vacuum pressure of about 975-985 mbar. This process leads to the formation of two seed fractions in the vessel: one sinking fraction and one floating fraction. The vacuum cycles continue until floating seeds are no longer sinking. The floating seeds are then removed and discarded. This process takes 20-30 minutes.

The seeds that sunk are then washed at running water during 10 minutes and dried. These are seed lots of commercial value that have been disinfected from BFB. They are further easily identifiable because the inside of the seed still contains traces of the disinfecting product.

From the 49 kg, the disinfected part represents 48 kg of seeds. In order to test the disinfection process, health test was performed on 40,000 seeds as follows:

10,000 seeds were tested by Polymerase Chain Reaction (PCR) assay according to USDA National Seed Health System Cb1.2 Seminis Inc. PCR-Wash method. The standard protocol can be obtained from the National Seed Health System, a program authorized by USDA-APHIS and administered by the Iowa State University Seed Science Center to accredit both private and public entities to perform certain activities needed to support the issuance of Federal phytosanitary certificates for the international movement of seed. See page 56 of the May 2014 edition of the "Vegetable Crop Method-Reference Manual B" National Seed Health System available at http://www.seedhealth.org/files/pdf/Vegetable_Crops.pdf.

20,000 seeds were tested by seedling grow-out assay according to USDA National Seed Health System Cb1.1 Seedling Grow-out method which is known and can be obtained from the National Seed Health System.

10,000 seed were tested by a sweat box assay which is similar to the previous grow-out assay but whereby seeds are sown in closed containers under growth chamber conditions optimal for the disease to develop. The seedlings are then tested similarly to the grow-out method.

None of the seeds was found infected while, on the contrary, the floating fraction represents about 1 kg and is tested positive for BFB (sweat-box assay at 10,000 seeds).

Germination was counted at 4 & 7 days with results of 99%/99% for the heavy fraction and 96%/92% for the floating fraction (Germination test according to Annex to chapter 5, International Rules for Seed Testing, International Seed Testing Association, Zurich, Switzerland, 1996).

Example 3: Disinfection of Cucumber Seeds Naturally Infected by Cucumber Green Mild Mottle Virus (CGMMV)

In this case, cucumber seeds have been obtained from a commercial seed lot, naturally infected by CGMMV in the production field.

The seeds were disinfected by standard method and by vacuum infiltration method. In this case, vacuum is applied at maximal pressure of 975-985 mbar from the beginning. This process leads to the formation of two seed fractions in the vessel: one sinking fraction and one floating fraction. The vacuum cycles continue until floating seeds are no longer sinking. The floating seeds are then removed and discarded. This process takes 15-20 minutes.

In this case two chemicals were used. Tri Sodium Phosphate at 10% by standard disinfection (A) and by vacuum infiltration (B), Na-Dichloroisocyanurate at 0.4% by standard disinfection (C) and by vacuum infiltration (D) See table I for CGMMV ELISA assay results and germination results.

We also tested the effect of different concentration of Na-Dichloroisocyanurate applied by vacuum infiltration on CGMMV and germination (table II) treatment E is untreated control; treatment F is vacuum infiltration of Na-Dichloroisocyanurate 0.75%; treatment G is vacuum infiltration of Na-Dichloroisocyanurate 1.5% and treatment H is vacuum infiltration of Na-Dich loroisocyanurate 2.0%.

TABLE I

CGMMV infection as tested by ELISA assay

| Treatment | ELISA assay result (rate of extinction at $A_{405}$) | Germination % |
| --- | --- | --- |
| Negative control | 0.13 | |
| A | 0.34 | 100 |
| B | 0.19 | 100 |
| C | 0.45 | 96 |
| D | 0.25 | 100 |

TABLE II

CGMMV infection as tested by ELISA assay

| Treatment | ELISA assay result (rate of extinction at $A_{405}$) | Germination % |
|---|---|---|
| Negative control | 0.13 | |
| E | 0.72 | 100 |
| F | 0.17 | 100 |
| G | 0.13 | 100 |
| H | 0.16 | 100 |

CGMMV was tested by ELISA assay according to method 7-026 of the international rules for seed testing annex to chapter 7: seed health testing methods; International Seed Testing Association, Zurich, Switzerland, 2010.

The germination test was performed according to Annex to chapter 5, International Rules for Seed Testing, International Seed Testing Association, Zurich, Switzerland, 1996.

Example 4: Disinfection of Tomato Seeds Naturally Infected by Tobacco Mosaic Virus (ToMV)

Tomato seeds have been obtained from commercial seed lot, naturally infected by ToMV in the production field. The seed lots were previously disinfected 3 times by a standard method, without success (control).

In this case 30 grams of dry seeds were disinfected by vacuum infiltration method using 4 liters of 2% Virkon (potassium peroxomonosulphate 50%, sulphamic acid 5% and sodium alkyl enzene sulphonate 15%. Virkon is a registered trademark of Antec International Limited, a subsidiary of DuPont, USA).

The vacuum was applied while seeds were located in a perforated basket above the disinfectant solution in a closed chamber. A vacuum pressure was applied at maximal reachable vacuum pressure of about 975-985 mbar, followed by submerging the seeds into the solution and releasing the vacuum. Vacuum/de-vacuum cycles were repeated 4 times and at the end, all the seeds sunk. The seeds were collected, rinsed for 5 minutes and dried. Results: in all tomato seed lots ToMV level was reduced to 0% of the control level (see table III). Germination level was increased by 2% in one seed lot and decreased 5% in the other seed lot.

TABLE III

| | | Lesions | Germination |
|---|---|---|---|
| Tomatoes Seed Lot 1 | Control | 21 | 93 |
| Tomatoes Seed Lot 1 | Vacuum Infiltration | 0 | 91 |
| Tomatoes Seed Lot 2 | Control | 3 | 93 |
| Tomatoes Seed Lot 2 | Vacuum Infiltration | 0 | 88 |

ToMV was tested under ISHI rules (International Seed Health Initiative, see annex to Chapter 7: Seed Health Testing Methods 7-028: Detection of infectious tobamoviruses on *Lycopersicon esculentum* (tomato) by the local lesion assay (indexing) on *Nicotiana tabacum* plants. p 1-10, published by The International Seed Testing Association (ISTA) Zürichstr. 50, CH-8303 Bassersdorf, Switzerland. Jan. 1, 2013).

The germination test was performed according to AOSA rules Testing Seeds (Volume 1 Principles and Procedures, Table 6A. Methods of testing laboratory germination. p. 6-55, *Solanumn lycopersicum* var. *lycopersicum* (tomato), published by the Association of Official Seed Analyst's (AOSA) 1601 52nd Avenue, Suite 1, Moline, IL 61265 USA, Oct. 1, 2012).

Example 5: Standard Na-Dichloroisocyanurate Disinfection (External Wash)

Species: Melon or Watermelon
The process: 10 kg of seed are added to 45 liters of 1% or 2% Na-Dichloroisocyanurate. The seeds are mixed in the solution for 30 minutes and then washed in running water for 10 minutes and then dried to the original water content.

Example 6: Disinfection of Melon Seeds Naturally Infected by Bacterial Fruit Blotch by Reduced Vacuum Pressure Melon seeds naturally infected by BFB were disinfected twice by the standard disinfection protocol as described in example 5 and were still found to be BFB infected.

Three batches of 1 kilograms of this seed lot were put in a 10 liter glass vessel together with 3.0 liters of disinfecting solution comprising of Na-Dichloroisocyanurate at 1.0%. Thirty cycles of vacuum/de-vacuum (each cycle having a duration of 1 to 1.5 minutes) were applied with three different level: (i) level A: full vacuum up to 975-985, (ii) level B: medium level of 740-816 mbar, and (iii) level C: low level of 576-667 mbar. After 40 minutes (i.e. after achieving the 30 cycles of vacuum/de-vacuum) the floating fractions were discarded and the sinking fractions were collected, washed for 40 minutes and dried.

Five thousand seeds of each treatment level (A, B, C) were tested and found negative for BFB by Polymerase Chain Reaction (PCR) method according to USDA National Seed Health System Cb1.4 Monsanto improved PCR method. The standard protocol can be obtained from the National Seed Health System, a program authorized by USDA-APHIS and administered by the Iowa State University Seed Science Center to accredit both private and public entities to perform certain activities needed to support the issuance of Federal phytosanitary certificates for the international movement of seed. See page 69 of the May 2014 edition of the "Vegetable Crop Method-Reference Manual B" National Seed Health System available at http://www-.seedhealth.org/files/pdfVegetable_Crops.pdf.

Example 7: Disinfection of Watermelon Seeds Naturally Infected by Cucumber Green Mild Mottle Virus (CGMMV)

0.150 kg watermelon seeds have been obtained from a commercial seed lot naturally infected by Cucumber Green Mild Mottle Virus (CGMMV) in the production field. This sample was put in a 1 liter glass vessel together with 0.5 liters of disinfecting solution comprising of Na-Dichloroisocyanurate at 0.2%. Vacuum was applied and build up to about 700 mbar then released. This process of vacuum/de-vacuum is repeated, each time with an increase of the vacuum pressure by approximately 50 mbar, up to the maximum vacuum pressure of approximately 985 mbar. This process continued for 40 minutes than the sinking fraction was collected. CGMMV was tested on 2000 seeds and found negative by ELISA assay according to method 7-026 of the international rules for seed testing annex to chapter 7 (Seed health testing methods; International Seed Testing Association, Zurich, Switzerland, 2010).

Example 8: Disinfection of Tomato Seeds Naturally Infected by CMM (*Clavibacter michiganensis* subsp. *Michiganensis* Using Ca(ClO)2 Treatment Tomato seeds have been obtained from commercial seed lot naturally infected by CMM in the production field. Vacuum treatment was done by vacuum infiltration (VI) method using 4 liters of 1% calcium hypochlorite, as described hereafter. The vacuum was applied while seeds were located in a perforated basket above the disinfectant solution in a closed chamber. A vacuum pressure was applied at maximal reachable vacuum pressure of about 975-985 mbar, followed by submerging the seeds into the solution and releasing the vacuum. Vacuum/de-vacuum cycles were repeated 4 times and at the end, all the seeds sunk. The seeds were collected, rinsed for 5 minutes and dried. Soaking treatment was done in the same solution for one hour after VI treatment or without VI treatment.

The germination tests have been done according to the Association of Official Seed Analysts (AOSA) (http://www.aosaseed.com/).

*Clavibacter michiganensis* subsp. *michiganensis* infection results were obtained by using the "method for the detection of *Clavibacter michiganensis* subsp. *michiganensis* on tomato seed" according to the International Seed Federation (ISF) Manual of Seed Health Methods, as can be found in the internet site: http://www.worldseed.org/isf/ishi_vegetable.html.

All the results are presented in the Table IV below.

TABLE IV

| Chemical | Treatment | CMM infection results | EN | OG | UT | UNIF |
|---|---|---|---|---|---|---|
| 1% Ca(ClO)2 | VI alone | Negative | 96 | 96 | 94 | 91 |
| | 1 hr soak alone | Positive | 98 | 98 | 95 | 92 |
| | VI then 1 hr soak | Negative | 99 | 99 | 92 | 89 |

VI: vacuum infiltration, EN: Energy = Early germination counts taken on Day 5 after planting in rolled towels), OG: Optimum Germination = Germination counted on Day 14 after planting in rolled towels, UT: Useable Transplants = Planted in trays in a greenhouse. Counts of seedlings deemed as useable to a commercial grower, UNIF: Uniform Transplants (UNIF) = Planted in trays in a greenhouse. Counts of seedlings that are deemed to be uniform in size.

Example 9: Disinfection of Cucumber Seeds Naturally Infected by Cucumber Green Mild Mottle Virus (CGMMV)

In this case, a commercial cucumber seed lot (2 kg) naturally infected by CGMMV was treated. The infected seeds were put into a reactor containing 20 liters of Na-Dichloroisocyanurate at 1.33%. The vacuum/de-vacuum cycles (i.e. vacuum infiltration) were applied gradually starting at 500 mbar and increased by 50 mbar each cycle up to the maximum of 985 mbar. Then we continued vacuum/de-vacuum cycles at maximum vacuum pressure of 985 mbar for a total of 30 cycles. This process leads to the formation of two seed fractions in the vessel: one sinking fraction and one floating fraction. Both fractions were separately collected. This process took 45 minutes. CGMMV was tested by ELISA assay according to method 7-026 of the international rules for seed testing annex to chapter 7: seed health testing methods; International Seed Testing Association, Zurich, Switzerland, 2010.

The germination test was performed on petri dishes (TOP) at 24 C incubator and root protrusion was counted at 4 days after seeding (TOP at 4 d).

The results are presented in Table V below.

TABLE V

| | Seed health lab results | | | % | |
|---|---|---|---|---|---|
| | | Out of 10 or 30 replicates | | Germination | |
| Treatment description | Cut-off = 2 × neg. cont | Average count | Positive/ total | TOP at 4 d | Remarks |
| Control - untreated | 0.130 | 0.841 | 10/10 | 97 | Contaminated |
| VI disinfection - sinking fraction (95%) | 0.130 | 0.081 | 0/30 | 94 | Clean |
| VI disinfection - floating fraction (5%) | 0.130 | 0.543 | 9/10 | 62 | Contaminated |

VI: vacuum infiltration.

Example 10: Disinfection of Cucumber Seeds Naturally Infected by Cucumber Green Mild Mottle Virus (CGMMV)

Samples of two commercial cucumber seed lots naturally infected by CGMMV in the production field were treated by standard disinfection or by vacuum infiltration methods. All treatments were done on 1500 seed in 300 ml solution for 40 minutes, followed by 40 minutes wash under running water. For the standard disinfection we used 2.5% Na-Dichloroisocyanurate solution and for the vacuum infiltration we used a solution containing 1.5% Na-Dichloroisocyanurate. The vacuum/de vacuum cycles were applied gradually starting at 500 mbar and increased by 100 mbar each cycle up to the maximum of 985 mbar. Then we continued vacuum/de-vacuum cycles at maximum vacuum pressure of 985 mbar for a total of 30 cycles. At the end of the treatment the floating seeds were discarded and the heavy fraction was collected, washed and dried for testing.

CGMMV was tested by ELISA assay according to method 7-026 of the international rules for seed testing annex to chapter 7: seed health testing methods; International Seed Testing Association, Zurich, Switzerland, 2010. The germination test was performed on petri dishes (TOP) at 24 C incubator and root protrusion was counted at 4 days after seeding (TOP at 4 d).

The results are presented in table VI.

TABLE VI

Seed health results: ELISA test on 1000 seed, 100 seeds per replicate

| Cucumber seed | | Cut-off = | 10 replicates results | | % | |
|---|---|---|---|---|---|---|
| Seed lot | Treatment description | 2 × neg. control | Average count | Positive/ total | Germination TOP at 4 d | Remarks |
| A | Control - untreated | 0.174 | 0.693 | 10/10 | 100 | Contaminated |
| A | standard disinfection 2.5% Na-dichloroisocyanurate | 0.174 | 0.238 | 9/10 | 100 | Contaminated |
| A | VI disinfection 1.5% Na-dichloroisocyanurate | 0.148 | 0.072 | 0/10 | 100 | Clean |
| B | Control - untreated | 0.174 | 0.737 | 10/10 | 100 | Contaminated |
| B | standard disinfection 2.5% Na-dichloroisocyanurate | 0.156 | 0.177 | 4/10 | 100 | Contaminated |
| B | VI disinfection 1.5% Na-dichloroisocyanurate | 0.148 | 0.075 | 0/10 | 100 | Clean |

The invention claimed is:

1. A method of obtaining a seed lot with seeds essentially free of seed-borne pathogens, comprising:
   a) placing seeds and a disinfecting solution into a vacuum reactor; wherein the seeds are submerged into the disinfected solution either prior or after the step b),
   b) applying vacuum pressure;
   c) releasing the vacuum pressure;
   d) reiterating steps b-c at least once; and
   e) collecting a sinking fraction of the seeds but not a floating fraction of the seeds, wherein said sinking fraction contains disinfected seeds,
   wherein step e) is carried out after each cycle of steps b-c or at the end of the reiterating steps;
   thereby obtaining a seed lot with seeds essentially free of seed-borne pathogens,
   wherein the disinfected seeds of the seed lot have a germination rate of at least 85% as determined according to the germination test of the annex to Chapter 5 of the International Rules for Seed Testing, International Seed Testing Association, Zurich, Switzerland, 1996;
   wherein the vacuum pressure applied at step b is between 400 and 985 mbar, and
   wherein the method does not comprise a soaking step of more than 12 hours.

2. The method according to claim 1, wherein the sinking fraction is collected after each cycle of steps b-c.

3. The method according to claim 1, wherein performing steps a-e takes no more than 2 hours.

4. The method according to claim 1, wherein steps b and c are carried out under conditions suitable for obtaining two fractions of seeds, one sinking fraction and one floating fraction.

5. The method according to claim 1, wherein a plurality of cycles of steps b-c are carried out with increasing the vacuum pressure at each cycle.

6. The method according to claim 1, wherein said seeds are from
   (i) cucurbit species, or
   (ii) solanaceous species.

7. The method according to claim 1, wherein the disinfecting solution is a solution containing Na-dichloroisocyanurate.

8. The method according to claim 2, wherein performing steps a-e takes no more than 2 hours.

9. The method according to claim 4, wherein the vacuum pressure is increased by 100 mbar after each cycle of steps b-c.

10. The method according to claim 6, wherein said seeds are from cucurbit species and are selected from the group consisting of watermelon, melon, squash, pumpkin, cucumber, and gourd species.

11. The method according to claim 6, wherein said seeds are from solanaceous species and are selected from the group consisting of tomatoes, peppers and eggplants species.

12. The method according to claim 1, wherein the disinfecting solution is a solution containing at least 0.1% Na-dichloroisocyanurate.

13. The method according to claim 1, wherein steps b-c are reiterated until no new sinking fraction is observed at step c.

14. The method according to claim 1, wherein said seed-borne pathogens include fungi, bacteria, viruses, or viroids.

15. The method according to claim 1, wherein said seed-borne pathogens are selected from (i) *Pseudomonas savastanoi* pv. *phaseolicola* and *Xanthomonas axonopodis* pv. *phaseoli* in Bean, (ii) *Phoma* lingam and *Xanthomonas campestris* pv. *campestris* in Brassica, (iii) *Alternaria dauci*, *Alternaria radicina*, *Alternaria radicina* and *Xanthomonas hortorum* pv. *carotae* in Carrot, (iv) *Septoria apiicola* in Celery, (v) *Acidovorax valerianellae* in Cornsalad, (vi) *Acidovorax* spp., *Acidovorax avenae* subsp. *citrulli*, Squash mosaic virus, Cucumber green mottle mosaic virus, Cucumber fruit mottle mosaic virus and Melon necrotic spot virus in Cucurbit, (vii) Lettuce mosaic virus in Lettuce, (viii) Pea seed-borne mosaic virus, Pea early browning virus and *Pseudomonas syringae* pv. *pisi* in Pea, (ix) Tobamoviruses and *Xanthomonas* spp. in Pepper, (x) *Clavibacter* spp., *Clavibacter michiganensis* subsp. *michiganensis*, Pepino mosaic virus, Tobamoviruses, *Pseudomonas* spp. and *Xanthomonas* spp. in Tomato.

16. The method according to claim 1, wherein the vacuum pressure applied at step b is between 975-985 mbar.

17. The method according to claim 1, wherein the seeds are selected from seeds of vegetables, cereals or grasses.

18. The method according to claim 1, wherein the disinfecting solution comprises a chemical agent as a disinfectant.

19. The method according to claim 1, wherein steps b-c are reiterated until no new sinking fraction is observed at step c.

20. The method according to claim 1, wherein the method does not comprise any soaking step.

21. The method according to claim 1, wherein performing steps a-e takes no more than 30 minutes.

22. The method according to claim 1, wherein said seed-borne pathogens include fungi.

23. The method according to claim 1, wherein said seed-borne pathogens include bacteria.

24. The method according to claim 1, wherein said seed-borne pathogens include viruses, or viroids.

25. The method according to claim 1, wherein the seeds are selected from seeds of vegetables.

* * * * *